(12) United States Patent
Schaeffer et al.

(10) Patent No.: US 7,534,250 B2
(45) Date of Patent: May 19, 2009

(54) INTRODUCER SHEATH

(75) Inventors: Darin G. Schaeffer, Bloomington, IN (US); Bruce Gingles, Bloomington, IN (US); Jason Urbanski, Ellettsville, IN (US); Daniel J. Sirota, Bloomington, IN (US); Michael C. Hoffa, Ellettsville, IN (US)

(73) Assignee: Cook Critical Care, Bloomington, IN (US)

( * ) Notice: Subject to any disclaimer, the term of this patent is extended or adjusted under 35 U.S.C. 154(b) by 835 days.

(21) Appl. No.: 10/608,043

(22) Filed: Jun. 27, 2003

(65) Prior Publication Data

US 2004/0049222 A1 Mar. 11, 2004

Related U.S. Application Data

(60) Provisional application No. 60/472,370, filed on May 21, 2003, provisional application No. 60/392,668, filed on Jun. 28, 2002.

(51) Int. Cl.
*A61M 29/00* (2006.01)

(52) U.S. Cl. .................. 606/191; 606/198

(58) Field of Classification Search .......... 623/1.11; 606/108, 191, 194, 192, 193, 198, 200; 600/184, 600/193, 208; 604/164.01, 167.02, 167.03, 604/167.04, 165.01, 514; 128/856
See application file for complete search history.

(56) References Cited

U.S. PATENT DOCUMENTS

| | | | | |
|---|---|---|---|---|
| 3,693,624 | A | | 9/1972 | Shiley et al. |
| 3,721,229 | A | * | 3/1973 | Panzer .................. 606/198 |
| 3,789,852 | A | | 2/1974 | Kim et al. |
| 3,831,587 | A | * | 8/1974 | Boyd .................... 600/207 |
| 4,271,839 | A | * | 6/1981 | Fogarty et al. .......... 606/194 |
| 4,306,562 | A | * | 12/1981 | Osborne ................ 604/523 |
| 4,364,391 | A | | 12/1982 | Toye |
| 4,411,655 | A | * | 10/1983 | Schreck ............... 604/165.01 |
| 4,471,778 | A | | 9/1984 | Toye |
| 4,596,559 | A | | 6/1986 | Fleischhacker |
| 4,601,713 | A | * | 7/1986 | Fuqua .................. 604/514 |

(Continued)

FOREIGN PATENT DOCUMENTS

WO   WO 98/19730 A1   5/1998

(Continued)

OTHER PUBLICATIONS

R. Goharderakhshan, B. Schwartz, D. Rudnick, P. Irby III, and M. Stoller, "Radially Expanding Single-Step Nephrostomy Tract Dilator," *Elsevier Science Inc.*, Jul. 2001.

(Continued)

*Primary Examiner*—Julian W Woo
(74) *Attorney, Agent, or Firm*—Brinks Hofer Gilson & Lione (57) ABSTRACT

An apparatus and method for inserting an article into a body opening. A radially expandable introducer sheath is delivered in a non-expanded condition into a body opening. A release mechanism releases the introducer sheath from the non-expanded condition into a condition that permits radial expansion of the introducer sheath upon introduction of a medical device through the sheath into the body opening. An optional handle having a circumferential opening may be provided for withdrawing the sheath from the body opening, while leaving the medical device in place.

19 Claims, 9 Drawing Sheets

U.S. PATENT DOCUMENTS

| | | | |
|---|---|---|---|
| 4,710,181 A * | 12/1987 | Fuqua | 604/514 |
| 5,042,475 A | 8/1991 | LaBombard | |
| 5,058,580 A | 10/1991 | Hazard | |
| 5,098,392 A | 3/1992 | Fleischhacker et al. | |
| 5,139,511 A * | 8/1992 | Gill et al. | 606/198 |
| 5,141,497 A | 8/1992 | Erskine | |
| 5,167,634 A | 12/1992 | Corrigan, Jr. et al. | |
| 5,183,464 A | 2/1993 | Dubrul et al. | |
| 5,222,487 A | 6/1993 | Carr et al. | |
| 5,250,033 A | 10/1993 | Evans et al. | |
| 5,431,676 A | 7/1995 | Dubrul et al. | |
| 5,489,273 A | 2/1996 | Whitney et al. | |
| 5,741,234 A * | 4/1998 | Aboul-Hosn | 604/174 |
| 5,814,058 A * | 9/1998 | Carlson et al. | 606/191 |
| 5,862,801 A | 1/1999 | Wells | |
| 5,928,198 A | 7/1999 | Lester | |
| 6,080,174 A | 6/2000 | Dubrul et al. | |
| 6,083,207 A * | 7/2000 | Heck | 604/256 |
| 6,325,812 B1 | 12/2001 | Dubrul et al. | |
| 6,902,575 B2 * | 6/2005 | Laakso et al. | 623/1.11 |
| 2001/0012950 A1 | 8/2001 | Nishtala et al. | |
| 2001/0039430 A1 | 11/2001 | Dubrul et al. | |
| 2001/0049499 A1 | 12/2001 | Lui et al. | |
| 2003/0023259 A1 | 1/2003 | Dubrul et al. | |

FOREIGN PATENT DOCUMENTS

| | | |
|---|---|---|
| WO | WO 99/49796 A1 | 10/1999 |
| WO | WO 01/32257 A1 | 5/2001 |

OTHER PUBLICATIONS

B. Shekarriz, S. Gholami, D. Rudnick, Q. Duh, and M. Stoller, "Radially Expanding Laparoscopic Access for Renal/Adrenal Surgery," *Elsevier Science Inc.*, Jul. 2001.

United States Surgical, "VersaStep Plus Access System," *Tyco Brochure*, Norwalk, CT, 2002.

United States Surgical, "Step Reposable System," *Tyco Brochure*, Norwalk, CT, 2001.

* cited by examiner

INTRODUCER SHEATH

The present patent application claims the benefit of the filing date under 35 U.S.C.§119(e) of Provisional U.S. Pat. Application Ser. No. 60/392,668, filed Jun. 28, 2002, and Ser. No. 60/472,370, filed May 21, 2003.

BACKGROUND OF THE INVENTION

The present invention relates to an introducer sheath, and to a method for inserting an article into a body opening of a patient through the introducer sheath.

The insertion of medical instruments through a pre-dilated hole in a patient's body is often accomplished in relatively straightforward fashion. An axial force is exerted on the instrument, thereby forcing the instrument through the opening into the desired internal part of the body. In certain medical procedures, however, medical professionals may encounter difficulties when inserting an instrument through a pre-dilated hole. In these instances, the axial force causes an undesired axial extension of the opening and increases the trauma experienced by the patient at the site. This axial extension can be particularly problematic in certain medical procedures, such as a tracheostomy, where a dilator is advanced into the trachea through the pre-dilated hole to open the trachea for introduction of a tracheostomy tube. In this instance, the axial force exerted by the dilator may cause the trachea to collapse, thereby further increasing the trauma to the patient and preventing the establishment of proper ventilation. In order to minimize the possibility of a tracheal collapse, the physician must repeatedly insert and withdraw one or more dilators at incrementally greater distances and/or incrementally greater diameters until the desired dilated diameter is obtained. This process can be very time-consuming at the very time that prompt action may be critical to the patient's well-being.

Some manufacturers have attempted to minimize this problem by providing dilators having a hydrophilic external surface to reduce the amount of friction encountered upon dilation, and thereby reducing the amount of axial force that is exerted on the trachea. Although the use of such coated dilators is somewhat effective in reducing the amount of friction encountered during dilation, there remains a desire to even further reduce the forces exerted on the body opening during dilation, thereby further minimizing the trauma to the patient.

SUMMARY OF THE INVENTION

The present invention addresses the needs of the prior art by providing a method and apparatus for inserting an article into a body opening of a patient.

In one form thereof, the invention comprises a method for inserting an article into a body opening. The body opening is dilated, and a radially expandable introducer sheath is inserted into the dilated body opening. The article is inserted through the expandable introducer sheath, thereby radially enlarging the body opening. The introducer sheath is then withdrawn, while leaving the article in place in the body opening.

In another form thereof, the invention comprises a method for percutaneously inserting an article in a body opening. A wire guide is inserted into the body opening, and the opening is dilated by inserting a dilator mechanism over the wire guide. The dilator mechanism includes an outer cannula that has a lumen therethrough, and a dilator positioned within the lumen. The dilator is then withdrawn, while the outer cannula is left in the body opening. A radially expandable introducer sheath is delivered over the wire guide into the lumen of the outer cannula. The introducer sheath is delivered in a non-expanded condition, and includes a release mechanism for releasing the introducer sheath from the non-expanded condition. The outer cannula is then removed, leaving the introducer sheath in the body opening. The release mechanism is activated to permit radial expansion of the introducer sheath, and the article is inserted through the expandable introducer sheath, thereby radially expanding the sheath.

In still another form thereof, the invention comprises a radially expandable introducer sheath for enlarging a percutaneous opening. The radially expandable sheath comprises a sheath body that comprises a folded distal portion when the sheath is in a non-expanded condition and an extended distal portion when the sheath is in a radially expanded condition. The sheath also comprises an insertion member for holding the sheath body in the non-expanded condition.

In yet another form thereof, the invention comprises a radially expandable introducer sheath for use in the percutaneous insertion of an article in a body opening. The introducer sheath comprises a sheath body that can be aligned to provide an axial opening for passage of the article therethrough into the body opening. A handle is engaged with the sheath body. The handle comprises an axial opening that is aligned with the sheath body axial opening, and further comprises a perimetrical opening through which the sheath may be withdrawn from the inserted article in the body opening.

In another form thereof, the invention comprises an introducer sheath system for use in the percutaneous insertion of an article in a body opening. The introducer sheath system comprises an introducer sheath comprising a sheath body and an insertion cannula. A distal end of the sheath body is foldable within an inner lumen of the insertion cannula when the sheath is in a non-expanded condition, and extendable beyond said insertion cannula to permit radial expansion of said sheath. The introducer sheath optionally includes a handle. When present, the handle may have either a continuous circumference, or an opening along the circumference of the handle through which the sheath may be withdrawn from the article in the body opening. The introducer sheath system further comprises a dilator for dilating the body opening. The dilator optionally includes a peel-away sheath member that provides a passageway for the introducer sheath into the body opening.

DETAILED DESCRIPTION OF THE INVENTION

Figure 1:
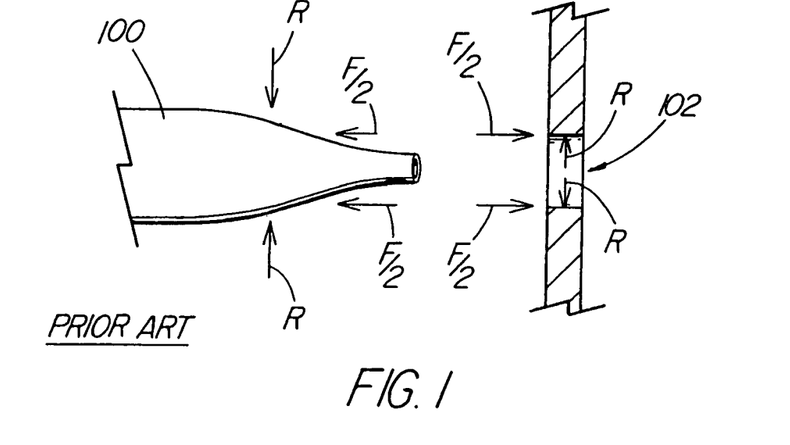
FIG. 1 is a side view of a prior art process for dilating a body opening.

FIG. 1 is a diagram illustrating the forces that are applied when a dilator 100 is used in the conventional fashion for dilating a body opening 102 of a patient. As shown in the figure, when dilator 100 is axially directed toward the body opening in the conventional manner, an axial force (F/2) is exerted on the body being dilated, and an equal but opposite force (F/2) is exerted on the dilator. The axial force exerted on the body opening results in the axial deformation of that opening in the direction of movement of the dilator, which deformation may cause discomfort and associated trauma to the patient. When certain body openings are being dilated, such as the trachea, the deformation may result in the collapse of that opening.

Figure 2:
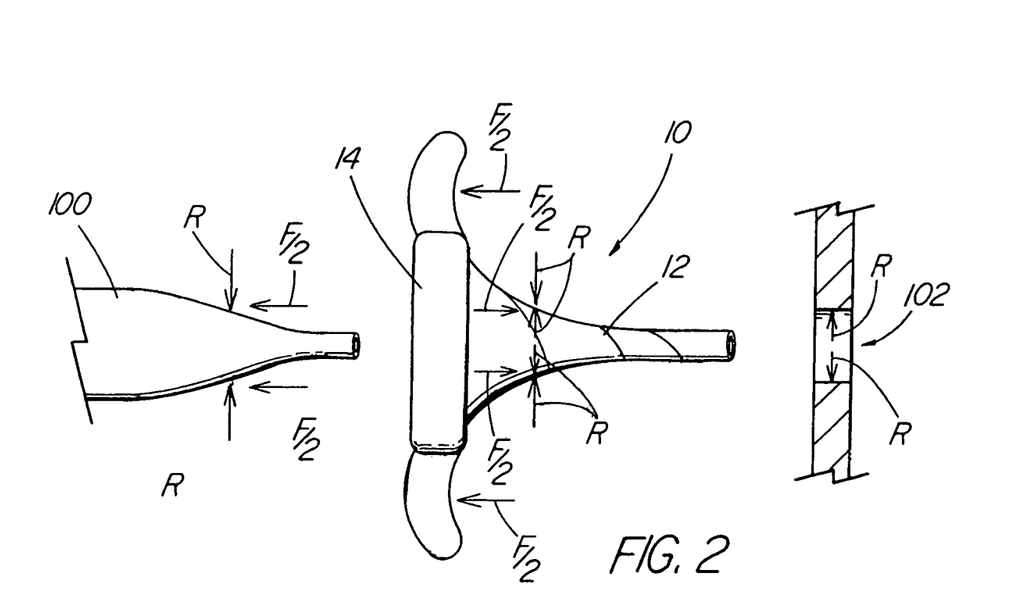
FIG. 2 is a side view of a process for dilating a body opening illustrating the use of an introducer sheath of the present invention.

FIG. 2 illustrates a view of a dilator and a body opening similar to that shown in FIG. 1. In this case, a radially expandable introducer sheath 10 is positioned between the dilator and the body opening. As used herein, the term "radially expandable" is used to refer to a sheath wherein the sheath body is capable of either expansion or displacement in the radial direction. The sheath body need not be formed of a material capable of expansion, as long as the material is capable of being displaced in a radial direction in response to a radially-directed force.

In the embodiment of FIG. 2, introducer sheath 10 comprises a sheath body 12 and a handle 14. As illustrated in FIG. 2, the use of the radially expandable introducer sheath in combination with the dilator 100 allows the body opening being dilated to be subjected primarily to radial forces (R), rather than axial forces as indicated in the conventional dilation shown in FIG. 1. The exertion of radial forces (R) on the body opening prevents substantial axial deformation of the body in the direction of the dilator, and thereby minimizes the potential adverse effects associated with such axial forces. Although FIG. 2 illustrates the use of introducer sheath 10 for insertion of dilator 100 into the body opening, other medical devices, such as a tracheostomy tube, may also be inserted into a body opening through sheath 10 instead of a dilator.

The introducer sheath 10 of the present invention is preferably formed from a sheath body 12 comprising a low friction non-rigid or semi-rigid material, such as a low friction fabric or polymeric material. The lack of rigidity enables the configuration of the sheath material to radially expand from a generally collapsed state prior to insertion of the medical device to an expanded shape during insertion of the device. Non-limiting examples of suitable material for the sheath body include polymers such as expanded polytetrafluoroethylene, polyethylene terephthalate (PET), polytetrafluoroethylene (PTFE) and synthetic polyamides such as nylon. To increase lubricity, the sheath body can also be coated with a hydrophilic coating, such as SLIP-COAT®, available from STS Biopolymers Inc.

The specific configuration of the introducer sheath is not critical, as long as it is capable of radial expansion in some manner from a non-expanded condition to a radially expanded condition when the medical device, such as a dilator or tracheostomy tube, is passed therethrough. Numerous designs are capable of such radial expansion and are considered within the scope of the invention. For example, the sheath body can be formed from an elastic or semi-elastic material that elastically expands to allow passage of the device, and thereafter reverts to a smaller size. Alternatively, the sheath in its non-expanded condition can have lateral folds in the nature of an uninflated balloon, or can have pleats, strips or other configurations that are capable of full or partial displacement in the radial direction in response to a radially-directed force.

Figure 3:
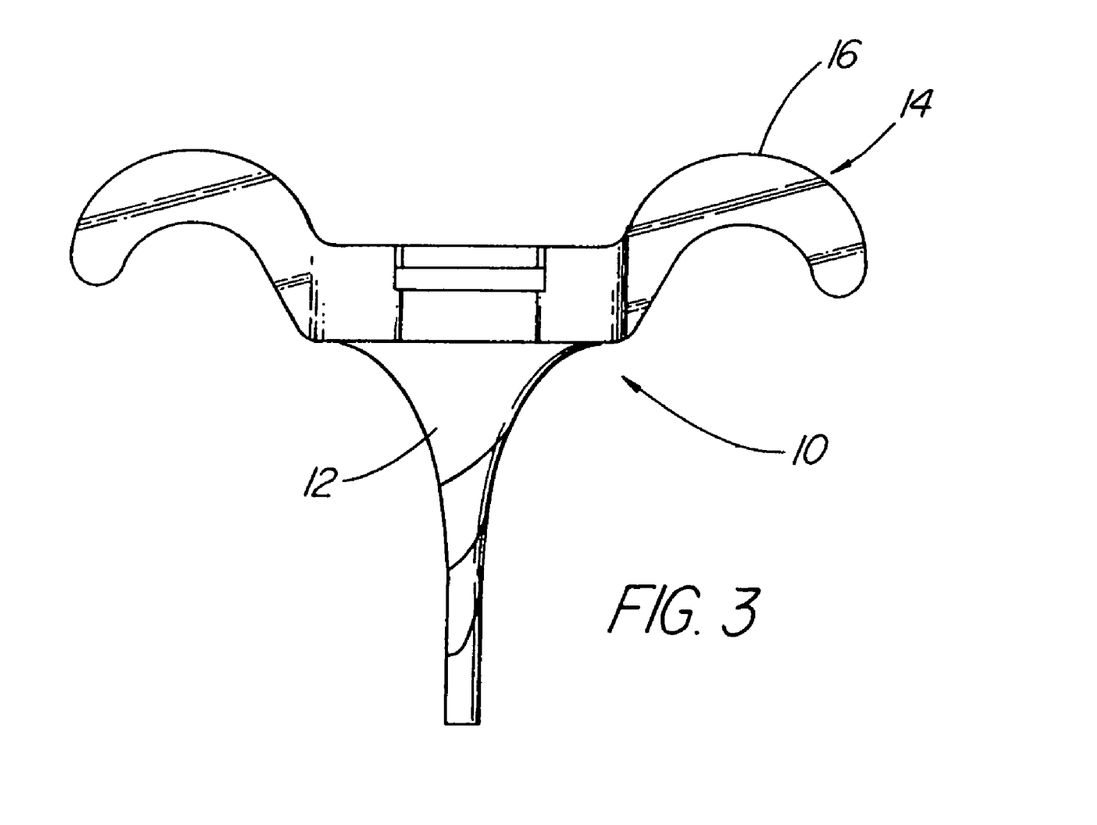
FIG. 3 is a side view of a preferred embodiment of an introducer sheath, illustrating a handle and a sheath body in a non-expanded condition.
Figure 4:
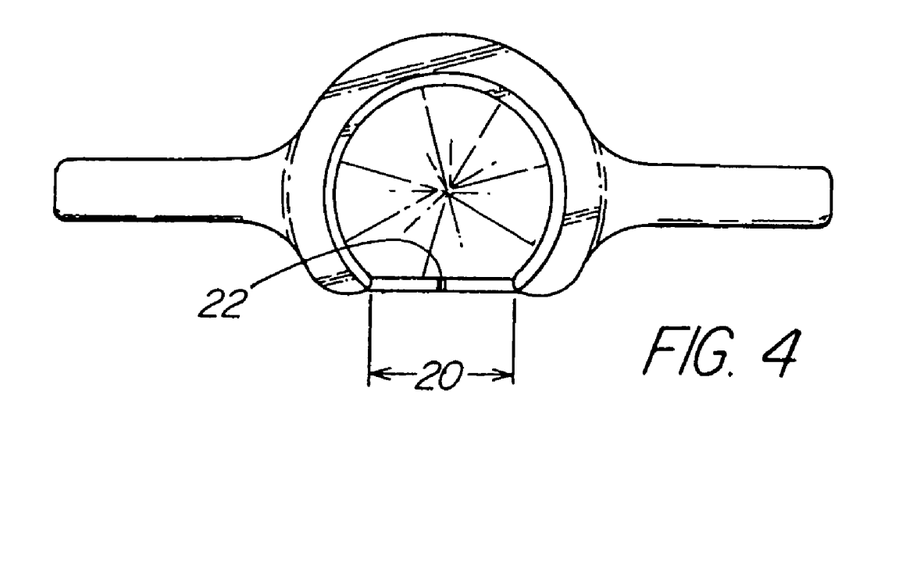
FIG. 4 is a top view of the introducer sheath of FIG. 3.

FIG. 3 illustrates a side view and FIG. 4 illustrates a top view of an embodiment of introducer sheath according to the present invention. In this embodiment, introducer sheath 10 includes sheath body 12 and handle 14. The proximal end of sheath body 12 has a large diameter for attachment to handle 14, while the distal end of sheath body 12 is wrapped in a manner such that it has a non-expanded, small diameter condition. Although these figures show that the small diameter configuration is formed by wrapping the distal end of the sheath body into this configuration, the invention is not so limited. Rather, any sheath body material that is capable of assuming a smaller diameter at its distal end and thereafter radially expanding to a larger diameter upon introduction of a medical instrument is within the scope of the invention.

Figure 5:
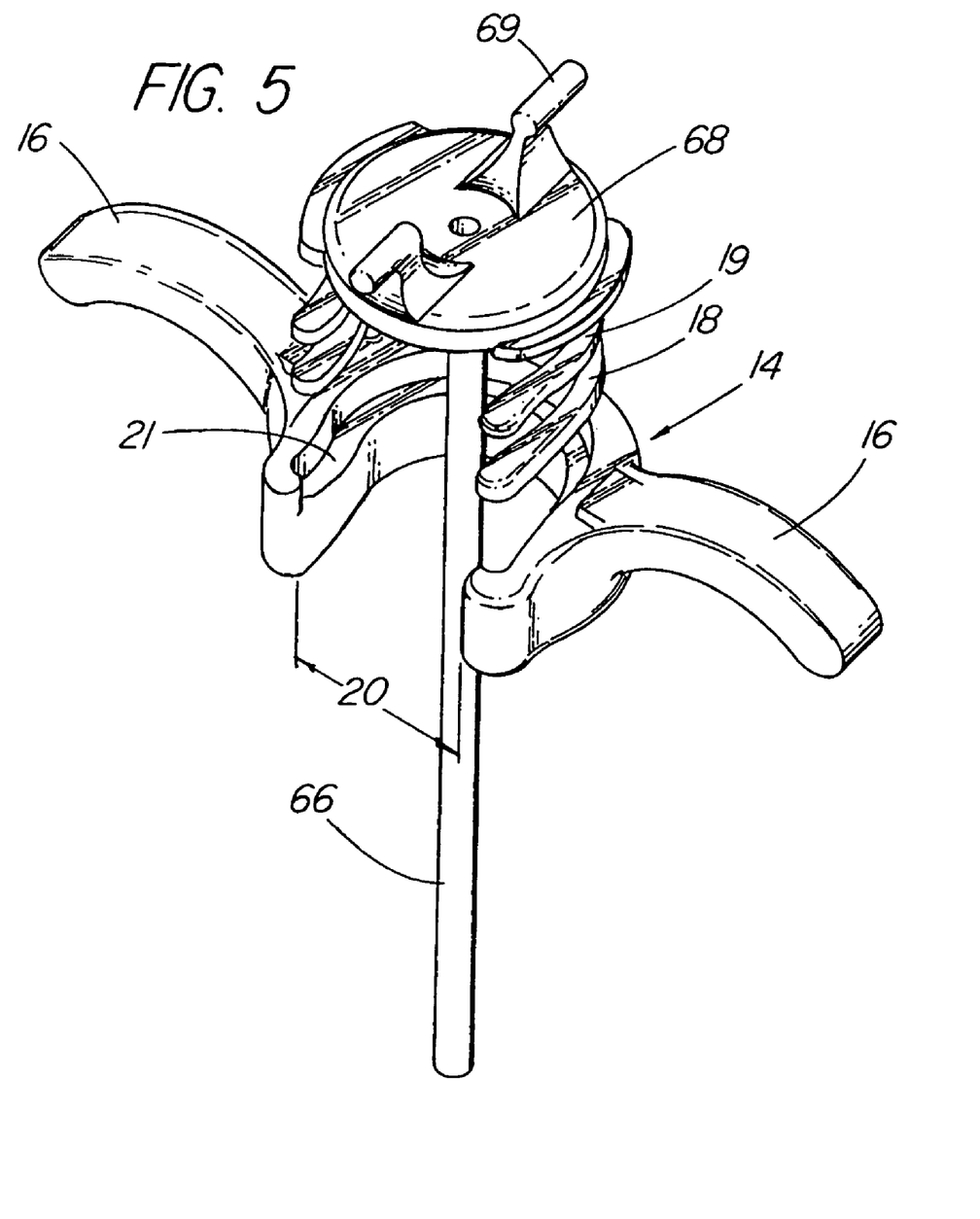
FIG. 5 is a perspective view of a handle showing the presence of rings for retaining the sheath body, and a pusher mechanism for inserting a wrapped sheath.

FIG. 5 is a perspective view of one type of handle that can be used with the sheath of FIGS. 3 and 4. Handle 14 includes supports 16 to support the fingers and/or thumb of the physician during use of the introducer sheath. Supports 16 provide enhanced control of the device and allow for ease of handling. In this embodiment, handle 14 includes one or more rings 18, 19 that may optionally be used to anchor the sheath in the handle. In the embodiment of FIG. 5, the upper portion of a sheath body can be wrapped around or otherwise secured to bottom ring 18. Bottom ring 18 is then fitted into the interior of handle 14, such as by resting on ledge 21. Upper ring 19 is then inserted to seal lower ring 18 and the wrapped portion of sheath body 12 in the device by means such as gluing or ultrasonic connection. Any convenient attachment mechanism may be used in place of ledge 21, such as one or more grooves along the inside surface of handle 14 into which the rings can be snapped for secure attachment. The handle shown has a generally C or U-shaped configuration. This configuration provides an open portion 20 along the handle circumference to allow easy removal of the introducer sheath once the medical device has been inserted into the body of the patient.

Figure 8:
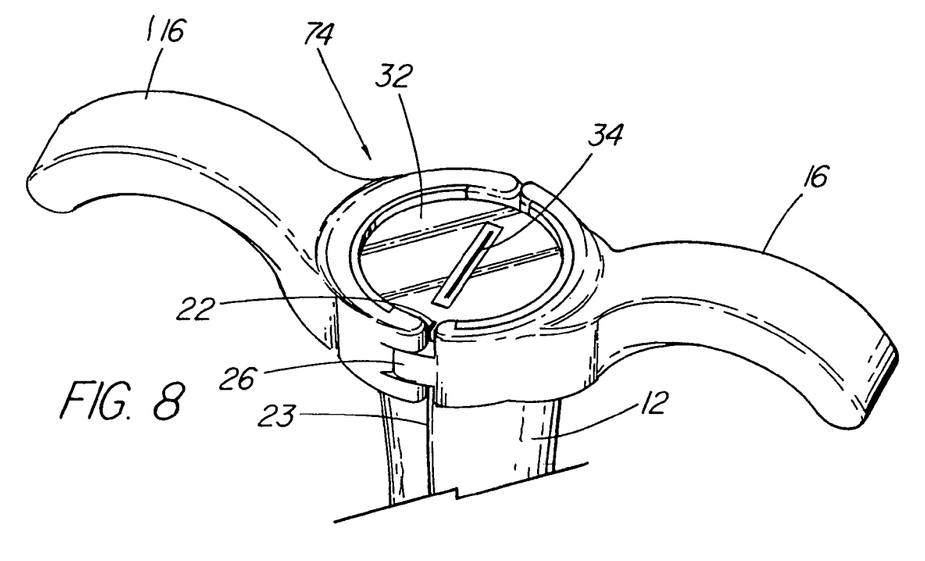
FIG. 8 shows an embodiment of an introducer sheath including a splittable hemostatic valve.

Preferably, sheath body 12 includes a weakened portion such as an axial slit 23 extending along the length of the sheath to facilitate removal of the sheath after insertion of the medical device by tearing along the axial slit. (FIG. 8.) When the handle is configured having an open portion 20 such as that shown, sheath 10 may be withdrawn from the body opening by simply laterally pulling the sheath to the side and tearing the sheath via the axial split. To facilitate tearing of the sheath at the axial split, the sheath can also be provided with a small knick 22. Knick 22 is useful to easily initiate the tear. After the sheath body is torn along the axial slit, the sheath may be removed, leaving the medical device in place in the body opening. Although the handle shown in FIGS. 3-5 is considered to have a generally "C" or "U" shape, this configuration is not critical. Other handle configurations that provide a perimetrical opening along the outer border, or perimeter, of the handle to facilitate removal of the sheath can likewise be used.

Although the embodiment shown in FIGS. 3-5 includes a perimetrical opening 20 in handle 14, it is not essential that the handle have an opening. Rather, the handle can be formed having a continuous geometric outer shape, such as a circular or rectangular shape. A continuous handle may be preferred when additional structural strength is desired in a handle.

Figure 6:
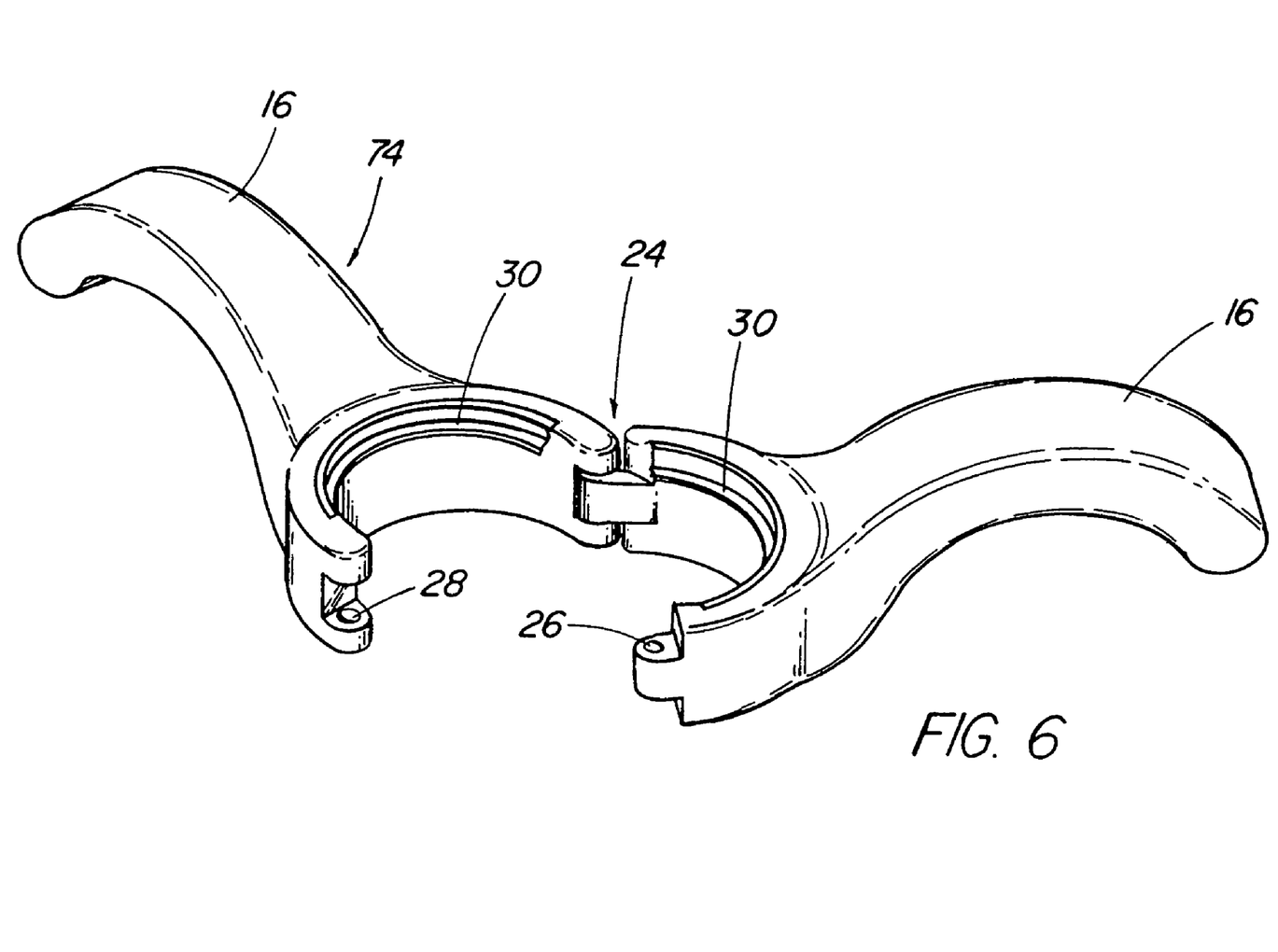
FIG. 6 is a perspective view of a continuous handle for an introducer sheath, showing the handle in the open position.
Figure 7:
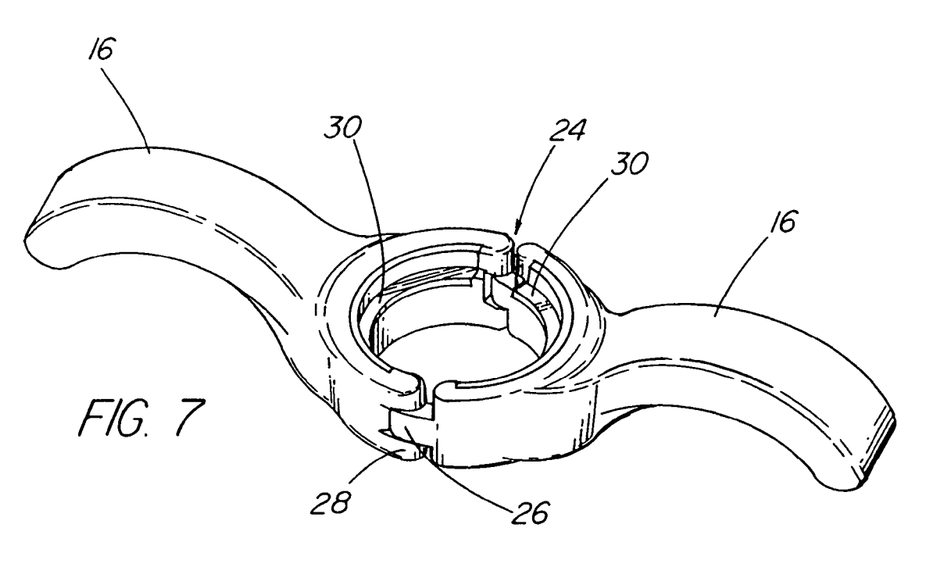
FIG. 7 is a perspective view of the handle of FIG. 6 in the closed position.

FIGS. 6 and 7 show an embodiment of a handle for an introducer sheath having a continuous handle. In the embodiment shown, handle 74 includes a pivot portion 24, such as a hinge, on one side and a complementary snap portion generally opposite the pivot portion. Any conventional arrangement for snapping, or closing, an opening may be utilized, such as the tab 26/receptacle 28 arrangement shown. The handle is shown in the open position in FIG. 6, and in the closed position in FIG. 7. The use of a closeable handle combines the benefits of a handle having a perimetrical opening for convenient removal of the medical device from the sheath with the strength of a continuous, closed handle. The hinge/tab combination enables the handle to be selectively "unsnapped" and pivoted open after the medical device has been inserted through the introducer. Any convenient attachment mechanism can be provided for attaching the proximal end of the sheath body to the handle. A sealing mechanism such as ledge 30 is provided. Ledge 30 may be used in conjunction with rings (not shown) around which the proximal end of sheath body 12 can be wrapped. Although the continuous handle shown in the figures includes structure enabling the handle to be selectively opened and closed, this feature is optional, and the continuous handle need not include this additional structure.

The composition of the handle is not critical. Generally, the handle can be formed from any rigid or semi-rigid material having sufficient structural strength for the purposes described. One example of such a material is a high-strength plastic. In addition, metals such as aluminum, stainless steel or metal alloys can be used, along with composite materials. The handle may be molded or machined such that the ledges, tabs or other attachment structure can be pressed into the component.

FIG. 8 shows a variation of an introducer sheath having a continuous handle, such as handle 74 in FIGS. 6 and 7. In this embodiment, the sheath includes a hemostatic valve member 32 having a slit, or valve, 34, for preventing leakage of body fluids through the introducer sheath. Hemostatic valves are well-known in the art, and can be formed of, for example, silicone and polyisoprene. This sheath can be removed following insertion of the medical device in the same manner as the sheath of FIGS. 6 and 7. Preferably, this valve also includes a knick 22 or like feature adjacent the snap mechanism that allows the valve to peel away along an axial slit 23 as the handle is opened.

Delivery Mechanism for Introducer Sheath.

Figure 9:
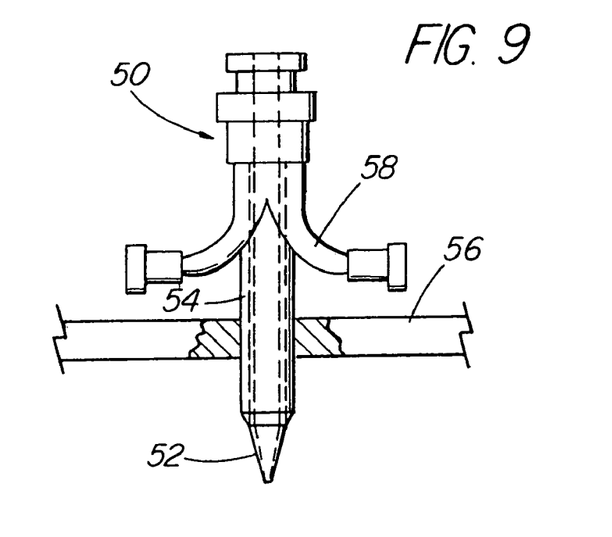
FIG. 9 shows a dilator/peel-away sheath arrangement for delivering the introducer sheath into the body opening.

Another aspect of the present invention comprises a mechanism for delivering the introducer sheath into the body opening. One embodiment of such a delivery mechanism is shown in FIG. 9.

Prior to dilating a body opening, the initial opening through the skin is normally made with a needle. A wire guide 60 is then inserted into the body opening over, or through, the needle. Following insertion of the wire guide, the needle is withdrawn and a dilator is advanced over the wire guide to dilate the initial opening in well-known fashion. A dilator/sheath combination 50 may be used for the dilation. Dilator/sheath combinations are known, and include a dilator 52 pre-loaded into a sheath 54. For convenience, it is preferred that the sheath is a peel-away sheath. In a preferred embodiment, the distal end portion of the dilator provides a smooth, or substantially smooth, transition to the distal end of the peel-away sheath so that the dilator/peel-away combination can be readily inserted, or punched, through the skin 56.

Figure 10:
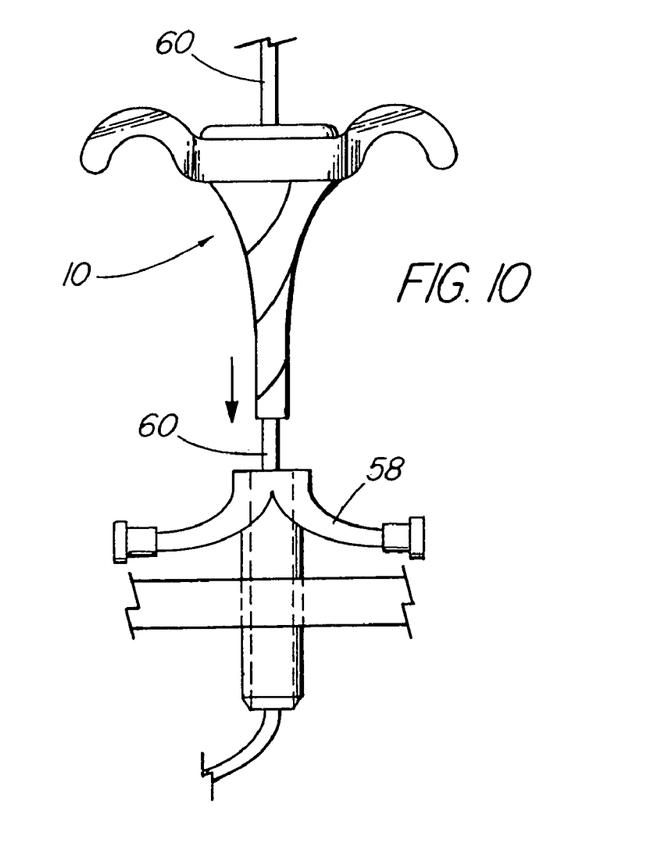
FIG. 10 illustrates an introducer sheath being delivered into the body opening over a wire guide.

After the opening has been dilated by punching dilator/sheath combination 50 through the skin, dilator 52 is withdrawn by sliding it over the wire guide 60. Introducer sheath 10 is then inserted through the lumen of the peel-away sheath in the direction of the arrow shown in FIG. 10. Peel-away sheath 54 is removed by peeling away petals 58 in well-known fashion, leaving radially expandable introducer sheath 10 in place in the body opening. Although it is preferred that a wire guide be used to guide the entry of the expandable sheath and other medical devices into the body opening, the use of a wire guide is not critical to the use of the inventive introducer sheath and the sheath may be utilized in the absence of a wire guide.

Release Mechanism for Introducer Sheath.

Figure 11:
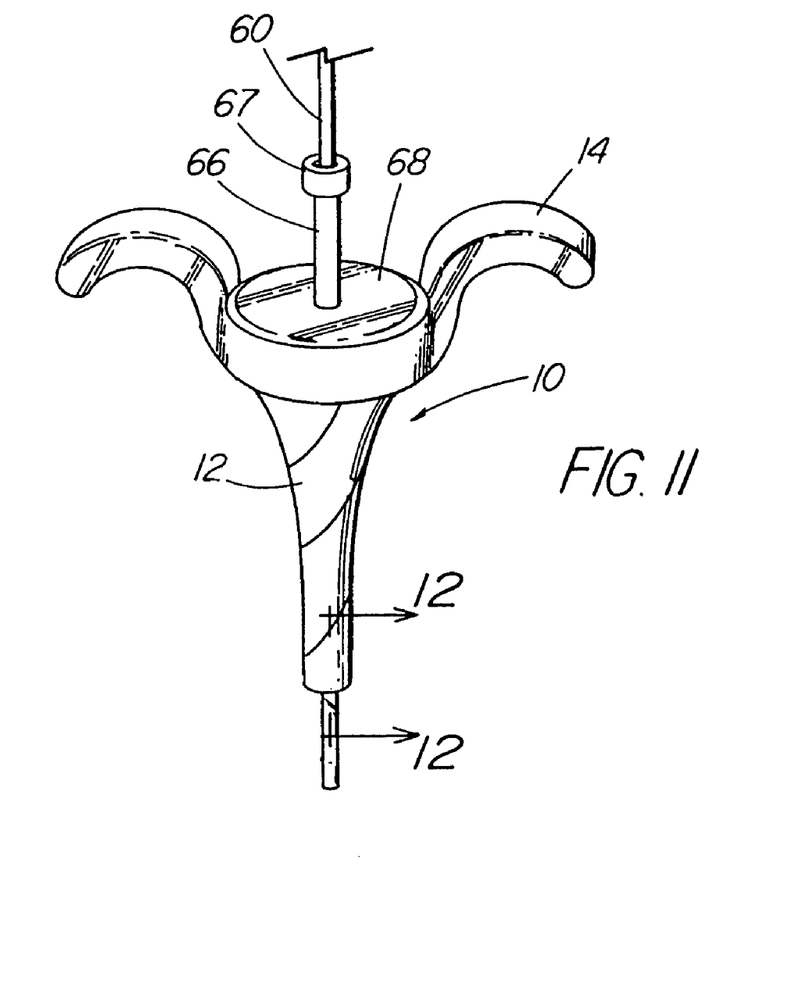
FIG. 11 is a perspective view of an introducer sheath in a non-expanded condition with a release mechansim.
Figure 12:
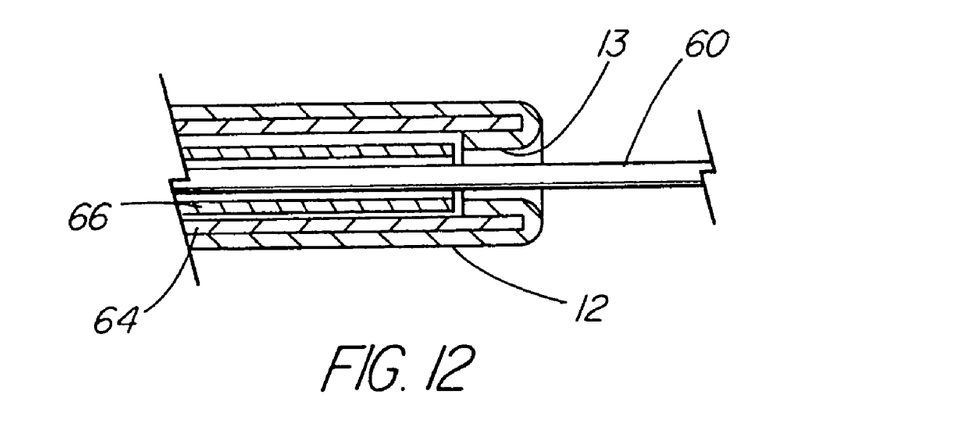
FIG. 12 is a sectional view taken along line 12-12 of FIG. 11.
Figure 13:
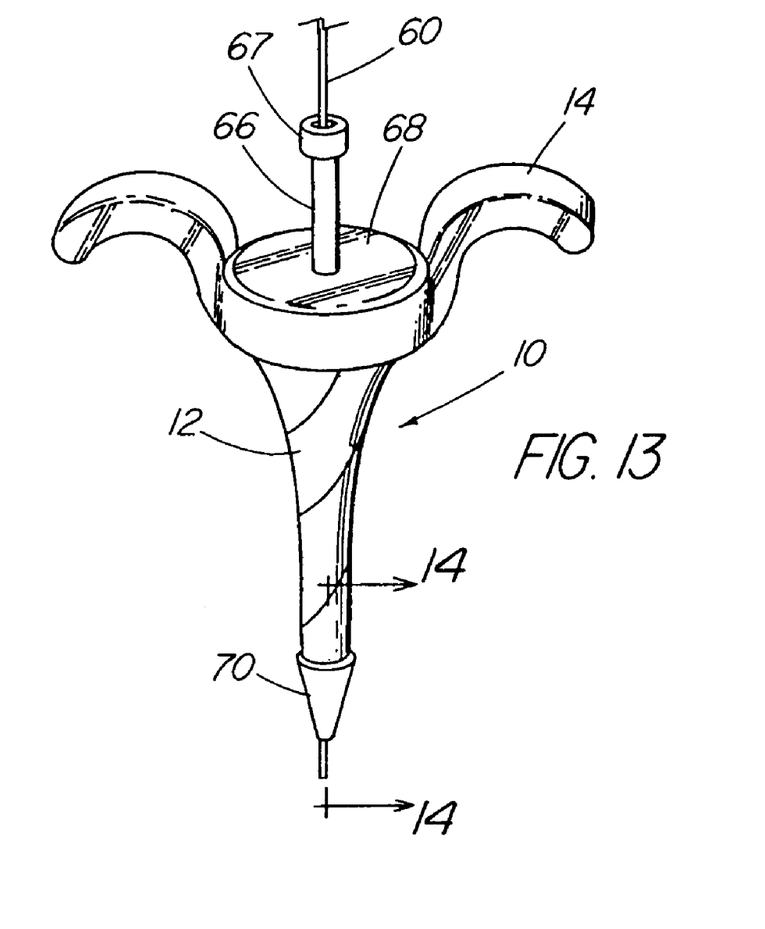
FIG. 13 is a perspective view of another embodiment of an introducer sheath in a non-expanded condition.

During delivery of the introducer sheath into the body opening, the sheath is retained in its non-expanded state so that it can be easily passed through the inner lumen of peel-away sheath 54. In the embodiment of FIGS. 11 and 12, the non-expanded state is achieved by wrapping the distal portion of the sheath into a smaller diameter configuration. Also, in this embodiment, the distal-most end 13 of sheath body 12 is folded in an inward direction, thus "sandwiching" this distal end between wire guide 60 and an insertion cannula 64. (FIG. 12) The introducer sheath is also provided with a pusher mechanism 66 and a cap 68, as shown in FIGS. 5, 11 and 13. Pusher mechanism 66 extends from proximally outside of cap 68 to the inwardly-wrapped distal portion 13 of sheath body 12 at the distal end of introducer 10. To release the distal portion of the sheath from the closed position shown in FIG. 11, pusher mechanism 68 is advanced by depressing knob 67. Pusher mechanism 68 forces distal end 13 of sheath body 12 out the distal end of insertion cannula 64, thereby releasing the sheath and permitting it to expand radially and thereby dilate the body opening when a device is axially inserted therethrough.

Insertion cannula 64 can be engaged with cap 68 in a manner such that insertion cannula 64, pusher mechanism 66 and cap 68 are releasable as a unit following release of the sheath. This can be accomplished, among others, by providing handle 14 and cap 68 with complementary screw threads, such that cap 68 can simply be unscrewed from handle 14, and the entire assembly comprising cannula 64, pusher mechanism 66, and cap 68 mechanism can be removed as a unit. Cap 68 in the embodiment of FIG. 5 includes optional tabs 69 to assist in unscrewing the cap. In an alternative embodiment, the pusher mechanism can be eliminated and/or it can be integral with the inner cannula. In this instance, the inner cannula can be structured such that it releases the distal end of the sheath material as it is advanced forwardly through the sheath. The insertion cannula, pusher and cap may be formed from any compatible rigid, or semi-rigid material having sufficient structural integrity to maintain its shape during use.

Figure 14:
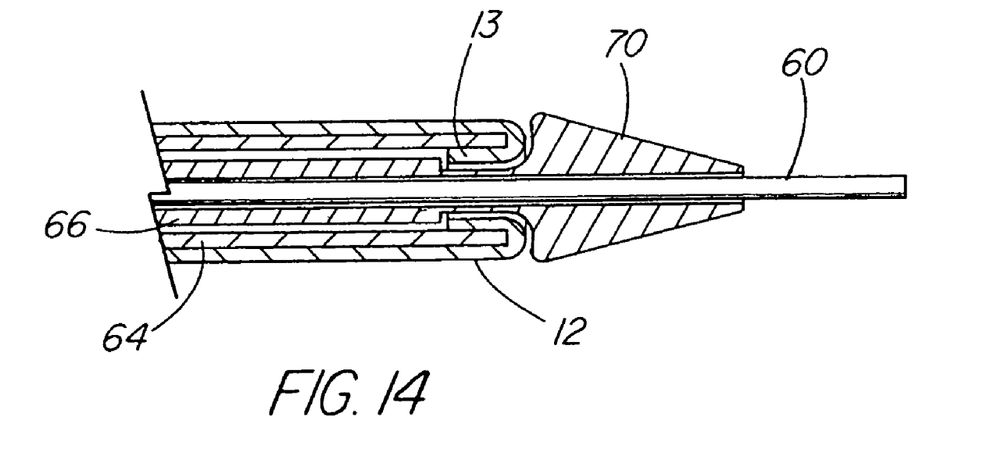
FIG. 14 is a sectional view taken along line 14-14 of FIG. 13.

In yet another embodiment, a dilator may be combined with the release mechanism. This embodiment is shown in FIGS. 13 and 14. Distal end 13 of sheath body 12 is held in place by sandwiching the material between wire guide 60 and insertion cannula 64, as described in the previous embodiment. In this embodiment, pusher mechanism 66 is engaged with a dilator tip 70 that extends through the distal end of introducer sheath 10. Preferably, dilator tip 70 is integral with pusher mechanism 66. This combined dilator/release mechanism can be inserted into the body opening directly over the wire guide, without the necessity of pre-dilation. After the device is inserted into the body opening, the pusher and dilator are advanced forwardly as described in the previous embodiment to release and radially expand the sheath material. The insertion cannula and the dilator/release mechanism can then be withdrawn through the expanded sheath.

Figure 15:
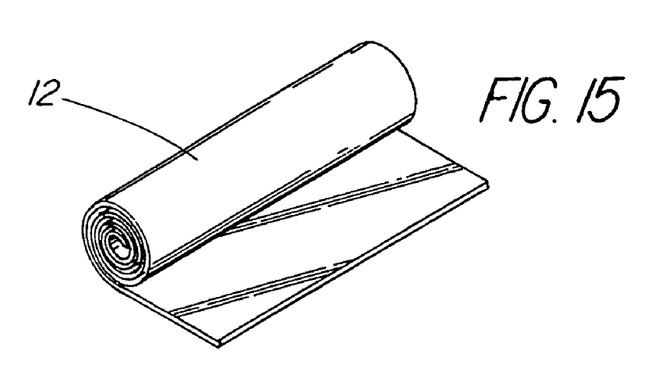
FIG. 15 is a perspective view of another alternative embodiment of a sheath body.
Figure 16:
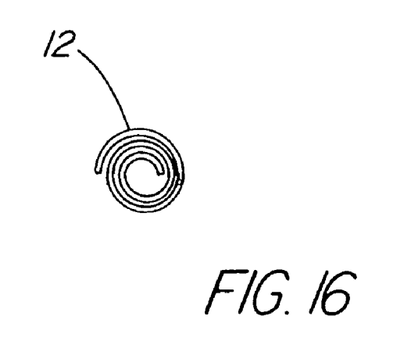
FIG. 16 is a side view of the embodiment of FIG. 15.

Although the examples shown above illustrate the presence of a handle 14 on the introducer sheath body, a handle is not necessary in all embodiments to achieve the radial expansion of the sheath. One embodiment of a sheath not having a handle is shown in FIGS. 15 and 16. In this embodiment, the sheath material 12 is rolled in a clock-spring configuration, which can then be inserted into the body opening. The dilator can then be axially inserted into the rolled-up sheath. As the dilator is advanced in the sheath, the sheath body unwraps in the radial direction to exert the radial force on the body opening. Other configurations permitting radial expansion of the body opening in the manner described may be substituted for those specifically described, and are considered within the scope of the invention.

Those skilled in the art will appreciate that the inventive concept is not limited to use in tracheostomy procedures, and that the device could be used anywhere in the body where a dilated hole is needed. Although in most instances it is believed that the inventive device will be used in external dilated body opening, the device can also be used in an internal hole, such as a stricture in a biliary tree, and the like.

While this invention has been particularly shown and described with reference to preferred embodiments thereof, it will be understood by those skilled in the art that various changes in form and details may be made therein without departing from the spirit and scope of the invention. Those skilled in the art may recognize or be able to ascertain using no more than routine experimentation, many equivalents to the specific embodiments of the invention described specifically herein, which equivalents are intended to be encompassed in the scope of the invention.

What is claimed is:

1. An introducer sheath for use in the percutaneous insertion of an article into a body opening, comprising:
    a sheath body configured to have an axial opening therethrough for passage of said article into said body opening, said sheath body selectively movable between a non-expanded condition and a radially expanded condition, said sheath body comprising a proximal portion and a distal portion, said proximal portion disposed along a proximal length of said sheath body, said distal portion comprising a folded portion when said sheath body is in said non-expanded condition and an extended portion when said sheath body is in said radially expanded condition;
    a hemostatic valve member engaged with said sheath body; and
    an insertion member receivable within said sheath body axial opening for holding said folded distal portion of said sheath body in said non-expanded condition, said insertion member extending within said sheath body axial opening at least substantially from said sheath body proximal portion to said sheath body distal portion, said insertion member comprising a cannula having an inner lumen, and said folded distal portion folded within said inner lumen.

2. The radially expandable introducer sheath of claim 1, further comprising a handle engaged with said sheath body.

3. The radially expandable introducer sheath of claim 2, wherein said handle comprises a perimetrical opening.

4. The radially expandable introducer sheath of claim 2, wherein the handle is generally C-shaped and comprises a circumferential opening.

5. The radially expandable introducer sheath of claim 2, wherein the sheath body comprises a low friction non-rigid material.

6. The radially expandable introducer sheath of claim 5, wherein the handle comprises one or more ring members for engaging said sheath body to said handle.

7. The radially expandable introducer sheath of claim 2, wherein said sheath body comprises an axial slit extending substantially along the length of the sheath body.

8. The radially expandable introducer sheath of claim 2, wherein the handle comprises a pivotable portion and a disengageable portion, said handle being selectively maneuverable between a closed position wherein said handle has a substantially continuous outer surface, and an open position wherein said pivotable portion is pivoted and said disengageable portion disengages such that an opening is defined for permitting withdrawal of said introducer sheath from said inserted article.

9. The radially expandable introducer sheath of claim 2, further comprising a pusher member structured and arranged for engaging said folded portion and for pushing said folded portion from said inner lumen to permit radial expansion of the introducer sheath.

10. The radially expandable introducer sheath of claim 1, wherein the sheath body comprises a member selected from the group consisting of expanded polytetrafluoroethylene, polyethylene terephthalate, polytetrafluoroethylene and nylon.

11. The radially expandable introducer sheath of claim 10, wherein the sheath body comprises expanded polytetrafluoroethylene.

12. An introducer sheath system for use in the percutaneous insertion of an article in a body opening, comprising:
    an introducer sheath comprising a sheath body and an insertion cannula, said sheath body having an axial opening therethrough for passage of said article, said insertion cannula receivable within said axial opening, said sheath body selectively movable between a non-expanded condition and a radially expanded condition, said sheath body having a proximal portion and a distal portion, said insertion cannula extending within said sheath body axial opening from said sheath body proximal portion to said sheath body distal portion, a distal end of said sheath body being foldable within an inner lumen of said insertion cannula when said sheath is in said non-expanded condition, and extendable beyond said insertion cannula to permit radial expansion of said sheath body; and
    a dilator engaged with said introducer sheath for dilating the body opening, said dilator having a tapered tip extending distal of said sheath body.

13. The introducer sheath system of claim 12, further comprising a sheath member for said dilator, wherein said sheath member provides a passageway for said introducer sheath into said body opening.

14. The introducer sheath system of claim 12, further comprising a pusher mechanism structured and arranged for engaging said foldable portion and for pushing said sheath body distal end from said non-expanded condition to permit radial expansion of said sheath body.

15. The introducer sheath system of claim 12, further comprising a pusher mechanism and a cap, said insertion cannula, pusher mechanism and cap comprising an assembly releasable as a unit from said system following radial expansion of said sheath body.

16. The introducer sheath system of claim 12, further comprising a handle engaged with said sheath body.

17. The introducer sheath system of claim 16, wherein said handle comprises a perimetrical opening.

18. The introducer sheath system of claim 16, wherein the handle is generally C-shaped and comprises a circumferential opening.

19. The introducer sheath system of claim 16, wherein the handle comprises a pivotable portion and a disengageable portion, said handle being selectively maneuverable between a closed position wherein said handle has a substantially continuous outer surface, and an open position wherein said pivotable portion is pivoted and said disengageable portion disengages such that an opening is defined for permitting withdrawal of said introducer sheath from said inserted article.

* * * * *